United States Patent [19]

Nicksic et al.

[11] Patent Number: 4,607,014

[45] Date of Patent: * Aug. 19, 1986

[54] EXPLORATION METHOD USING ELECTRON SPIN RESONANCE SIGNALS FROM HYDROCARBON CRUDE

[75] Inventors: Stephen W. Nicksic, Brea; George W. Starke, Calistoga, both of Calif.

[73] Assignee: Chevron Research Company, San Francisco, Calif.

[*] Notice: The portion of the term of this patent subsequent to Nov. 15, 2000 has been disclaimed.

[21] Appl. No.: 507,827

[22] Filed: Jun. 23, 1983

Related U.S. Application Data

[63] Continuation of Ser. No. 202,226, Oct. 30, 1980, abandoned.

[51] Int. Cl.$^4$ ...................... G01N 24/10; G01N 33/24
[52] U.S. Cl. ...................... 436/29; 324/316; 436/173
[58] Field of Search ............... 324/300, 303, 316, 323, 324/324; 436/173, 60, 29, 30, 31

[56] References Cited

U.S. PATENT DOCUMENTS

| | | | |
|---|---|---|---|
| 2,312,271 | 2/1943 | Smith | 23/230 EP |
| 3,719,453 | 3/1973 | Erdman | 23/230 EP |
| 3,740,641 | 6/1973 | Hwang et al. | 23/230 EP |
| 4,093,420 | 6/1978 | Grayson et al. | 23/230 EP |
| 4,415,671 | 11/1983 | Nicksic | 436/173 X |

OTHER PUBLICATIONS

Niizuma et al., *Fuel,* 1977, vol. 56, Jul. pp. 249–256.
Yen et al., "Analytical Chemistry", vol. 34, No. 6, May 1962, pp. 694–700.

*Primary Examiner*—Arnold Turk
*Attorney, Agent, or Firm*—S. R. LaPaglia; E. J. Keeling

[57] ABSTRACT

An exploration method is disclosed for mapping subsurface migration of crude petroleum by measuring electron spin resonance signals from materials within samples of the subsurface formations and identifying the samples that contain petroleum crude by detecting enhancement and/or suppression of the electron resonance signals due to the addition of a chemical material. Electron spin resonance signals from crude oil are enhanced by the presence of iodine and suppressed by the presence of ferric chloride.

2 Claims, 4 Drawing Figures

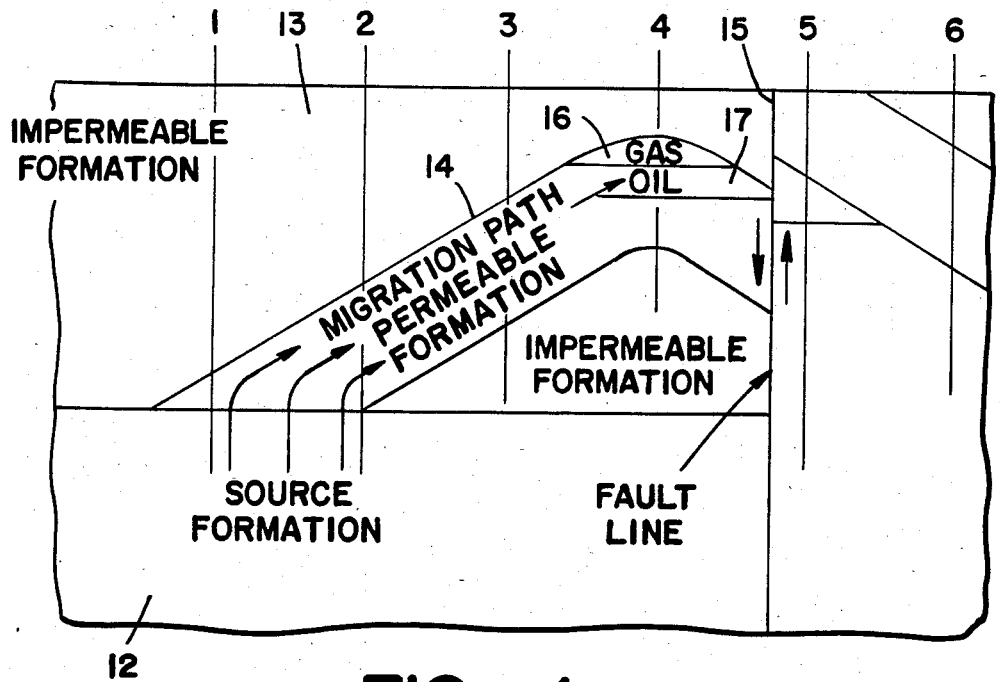
FIG_1
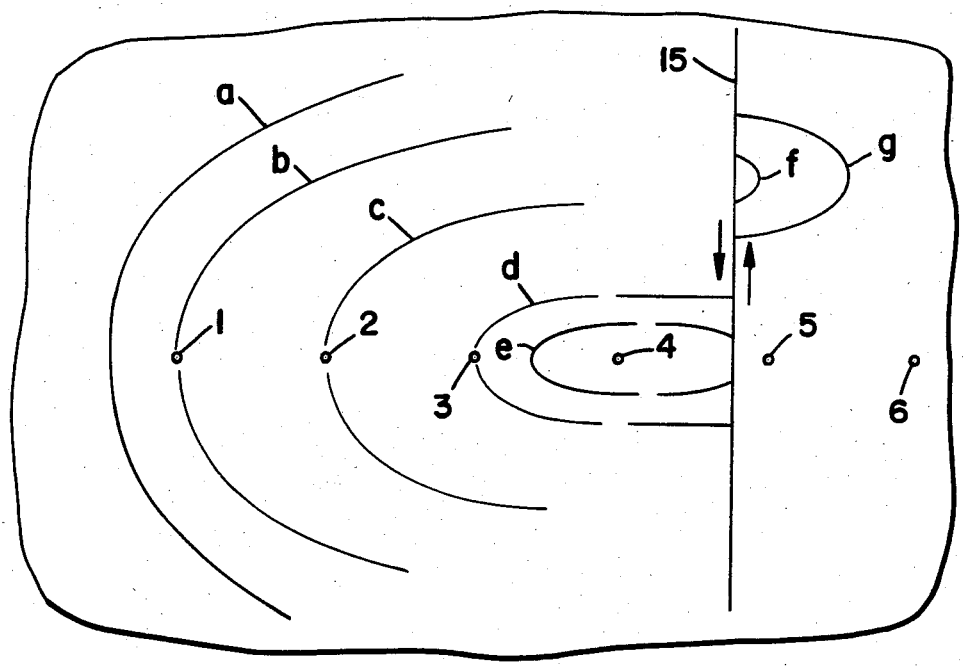
FIG_2

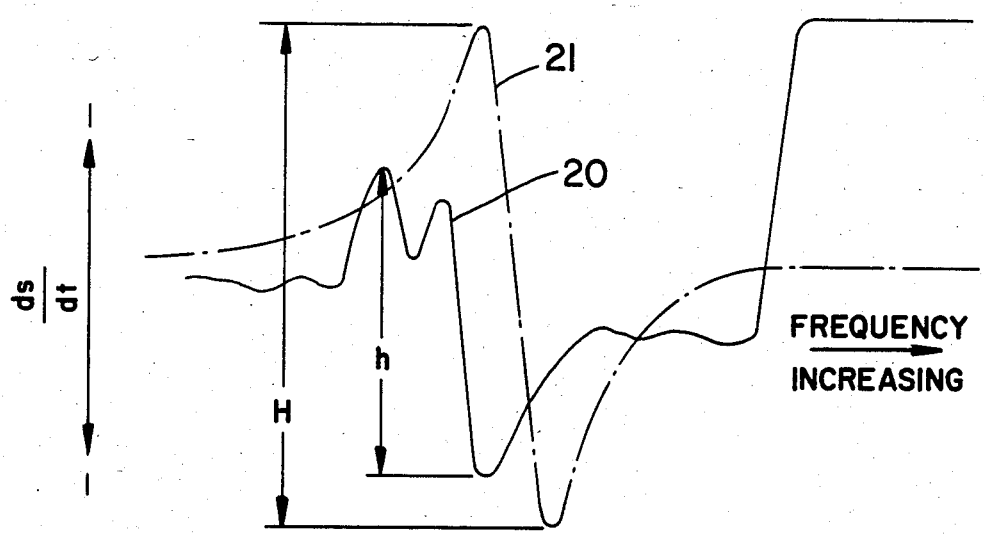
CRUDE OIL/ENHANCED CRUDE OIL
FIG_3
REFINED PRODUCT
NO EVIDENCE OF ENHANCEMENT
FIG_4

EXPLORATION METHOD USING ELECTRON SPIN RESONANCE SIGNALS FROM HYDROCARBON CRUDE

This is a continuation of application Ser. No. 202,226, filed Oct. 30, 1980, now abandoned.

BACKGROUND OF THE INVENTION

1. Field of the Invention

This invention relates to the detection of carbonaceous materials or materials geologically associated therewith. More particularly, it relates to the location of subterranean geological deposits of carbonaceous materials or materials geologically associated therewith, such subsurface earth formations are often referred to as source formations or migration paths. By "carbonaceous materials" as used herein is meant petroleum, coal, natural bitumens, including tars and asphalts, partially carbonized animal and vegetable matter and carbonaceous geological deposits and formations including oil-bearing shales. Further, this invention relates to a method for distinguishing crude petroleum carbonaceous materials from coal or shale carbonaceous materials on subsurface earth formation materials.

2. Prior Art

Prior to this invention, there has been no practical way of directly detecting the presence of very small quantities of carbonaceous materials on samples of subsurface earth formation materials. Further, if small quantities of such materials were detected, there was no practical way of positively distinguishing within such detected carbonaceous materials those materials which are crude petroleum based materials.

Representative of the prior art in the field of prospecting for petroleum are U.S. Pat. No. 2,686,108, W. S. Hoffmeister, issued Aug. 10, 1954, for Microfossil Prospecting for Petroleum, where a process is disclosed for identifying sediments from bore hole samples; U.S. Pat. No. 3,305,317, J. E. Cooper et al, issued Feb. 21, 1967, for Method of Prospecting for Petroleum, where a process is disclosed for analyzing ground waters for certain carbon atoms and comparing the ratio of certain of those identified carbon atoms as a means for identifying a petroleum reservoir; U.S. Pat. No. 3,343,917, G. M. Friedman, issued Sept. 26, 1967, for Obtaining Paleoenvironmental Information, where a process is disclosed for prospecting for petroleum by collecting and analyzing sedimentary rock for carbonate minerals; and U.S. Pat. No. 4,093,420, J. F. Grayson et al, issued June 6, 1978, for Mineral Prospecting By Organic Diagenesis, where a method of prospecting is disclosed for collecting and analyzing geological samples to produce anomalies characteristic of subsurface formations.

Each of the foregoing prior art methods measures a characteristic or a constituent that is representative of the presence of crude oil or is typical of the formations containing crude oil. None measure signals directly from crude oil itself.

Various methods are known for detecting the presence of carbonaceous materials, including, in increasing order of sensitivity, stain chemistry (adding chemicals to a sample to detect a change in color when carbonaceous materials are present); distillation treatment (as in chromatography where the presence of distillation fractions are detected); fluorescence (the irradiation with selected wave length electromagnetic energy to cause certain constitutents to fluoresce); and nuclear or electron spin resonance (the identification of spinning atomic particles in the constituents of the carbonaceous materials). The most sensitive of the foregoing techniques is electron spin resonance (ESR) where the presence of unpaired electrons in atomic structures are identified by subjecting samples of the structures to controlled magnetic and electromagnetic fields.

With the use of ESR techniques, it is possible to detect the presence of very small traces of carbonaceous materials; however, it is not possible to distinguish the type of carbonaceous material, i.e., crude petroleum, coal, tar sand or shale, from which the ESR signals were derived. ESR signals from geological materials may be attributable to a number of carbonaceous materials, both natural and refined, thus further confusing the attempt to identify a carbonaceous material.

The present invention uses ESR plus techniques for distinguishing the ESR signal of crude petroleum based natural carbonaceous materials as a method for detecting the presence or past presence of such materials in an exploration method.

SUMMARY OF THE INVENTION

Frequently subsurface accumulations of crude oils and gases are believed to have passed or migrated along formations from a source of the development of the hydrocarbon materials to the point where the gas and oil are accumulated below an impermeable formation. The location of these deposits of crude oil is usually based upon surface observations of geological formations or from the analysis of surface collected reflection seismographic information which is intended to provide the observer with the information concerning the subsurface formations. At its best, the geological information determined in the foregoing manner can supply the observer with a speculative construction for the subsurface formations.

After careful analysis has been performed to determine the subsurface geology, a decision is made to drill an exploratory well into the formations to attempt to contact the formation where hydrocarbon materials would be accumulated. During the course of the drilling, careful review is made in the form of well-logging techniques to determine what formations have been penetrated and what is the likelihood of the formation containing, presently or previously, certain hydrocarbon materials.

The process of attempting to find a subsurface accumulation of hydrocarbons is further complicated by the usual occurrence of faulting of the subsurface formations which may move portions of the formations both horizontally and vertically with respect to other portions, thus offsetting the possibilities that simple and continuous formations would occur. As a result, frequently a well drilled into a target may not really encounter the target because of a fault which may have moved certain portions of the formation from the location in which they had been predicted to be located. Having missed the target formation, it is desirable to know whether hydrocarbon materials had at least at one time passed through the formations, perhaps in the direction of another position for accumulation. The residual remaining in a formation may be minute quantities of the hydrocarbon materials and, in most cases, will be the heavy constituents, particularly the asphaltenes which remain in contact with surface layers of the subsurface formations.

The present invention provides a method for deriving information concerning minute traces of hydrocarbon or carbonaceous materials on the surfaces of formation materials so that an interpretation may be derived concerning the possibility that crude oil constituents have been formed in or passed through the formations encountered.

An object of the present invention is an exploration method for mapping the subsurface course of a crude petroleum where minute quantities of hydrocarbon constituents have been retained on a subsurface formation and wherein an electron spin resonance signal is derived from the formation materials and wherein the electron spin resonance signal is enhanced as a result of the introduction of iodine material into the formation.

A further object of the present invention is a method for distinguishing crude oil materials within a subsurface formation by the process of measuring electron spin resonance signals and the resultant enhancement of such electron spin resonance signals through the introduction of iodine to the formation.

Further objects and features of the present invention will be readily apparent to those skilled in the art from the appended drawings and specification.

BRIEF DESCRIPTION OF THE DRAWINGS

FIG. 1 is a representative cross-sectional view through an earth formation illustrating a possible formation upon which measurements of the type described in this invention might be performed.

FIG. 2 is a plan view representing the formation of FIG. 1.

FIG. 3 is a time vs. signal strength curve illustrating electron spin resonance signals produced in accordance with the present invention.

FIG. 4 is a time vs. signal strength curve of electron spin resonance signals measured from refined petroleum products and measured in accordance with the techniques of the present invention.

DETAILED DESCRIPTION OF THE DRAWINGS

FIG. 1 is a representative cross-sectional view through an earth formation and illustrates schematically a possible source formation 12 covered by an overburden 13 which includes a tilted migrational path 14 of permeable materials formed in the representative configuration of an anticline. A fault line 15 is intended to illustrate the possibility that formations to the left of the line 15 remain stationary, while those two at the right of the line have moved upwardly as illustrated in FIG. 1. At the upper end of the anticline of the formation 14, a portion is illustrated as a gas cap 16 and an oil or hydrocarbon accumulation at 17. The vertical lines numbered 1 through 6 are intended to represent wells drilled into the formation in an attempt to locate the possible accumulated gas and oil in the area 16.

FIG. 2 is a plan view representation of FIG. 1 with contour lines a, b, c, d, e, f, and g intended to represent the subsurface topography of the anticline of FIG. 1. The fault line 15 also illustrates that, in the examples shown, the formations to the left of the line 15 have remained stationary while the formations to the right of the line have been moved horizontally. The wells 1 through 6 are illustrated as penetrating in the formation from the surface.

FIGS. 1 and 2 are intended to permit the reader to understand that hydrocarbon formation materials may have been produced in one zone of the formation and may have migrated to another zone of the formation through permeable paths and may be trapped within the formation by an impermeable cover over the migration path. In the exploration and production of hydrocarbons from oil fields, it is often desirable to know where hydrocarbon materials have migrated and to identify migration paths in order to decide in which direction and at what distance another well might be drilled in order to find the hydrocarbon materials. In the very simplified case illustrated in FIG. 1, the source materials may have migrated up through path 14 from formation 12 past the location of wells 1, 2 and 3, but may not have migrated up through formations to the right of the fault block past the formations or the wells marked 5 and 6.

Prior art methods for identifying migration paths have been expensive to perform and difficult to interpret. In most cases, samples of the subsurface formations are brought to the surface and subjected to extensive laboratory analysis in order to identify minor quantities of migrating hydrocarbon crudes. In accordance with the present invention, samples of formations collected during the drilling of subsurface wells are analyzed by electron spin resonance techniques for the presence of residual asphaltenes which are left behind as mobil hydrocarbon crudes have been transported or migrated through a formation. In this regard, minute quantities of asphaltenes may provide readable electron spin resonance signals even though the migration through the formation may have occurred an extremely long time prior to the collecting of the sample and even though there are only small traces of the asphaltenes on the surfaces of the formation materials.

Electron spin resonance measurement equipment is readily available and may be provided at the well head during the drilling of an exploratory well. Such equipment is available from Varian Associates in the form of a device identified as Model E-3. The improvement of the present invention is to provide a means for identifying the electron spin resonance signals which apply only to residual hydrocarbon materials.

In a copending application of one of the present inventors, Ser. No. 202,102, filed Oct. 30, 1980, now U.S. Pat. No. 4,415,671 it has been disclosed that the signals from spinning electrons in unrefined hydrocarbons can be enhanced by the addition of certain halogen materials to the sample from which the signals are measured. In the invention herein disclosed, the enhancement of electron spin resonance signals is used in a method for identifying and locating the possible source of hydrocarbon generation within the formation and the migrational path of that material to a potential, producible accumulation.

In accordance with the method of the present invention, samples of subsurface earth formation materials are taken from wells drilled into the formation and these samples are analyzed by the measurement of electron spin resonance signals from the materials within the samples. The first signals measured are from the sample materials alone and then a second measurement is made while the sample is in the presence of an iodine solution. If the signal is substantially enhanced, it may be concluded that the material from which the first measurements were made did indeed contain crude hydrocarbon materials. Such analyses may be performed on samples taken from known positions within a formation along wells having known locations so as to map the presence of crude hydrocarbon materials and, from this mapping, it may be possible to produce a representation of the potential migration paths of hydrocarbon crudes within that formation.

The particular electron spin resonance signals measured from the formation samples are selected in a particularly narrow energy band width that represents the potential signals from asphaltenes, the residual material that is left behind as a crude petroleum migrates through a formation. While the selected samples may have been contaminated by other hydrocarbon materials, and, the other hydrocarbon materials might have produced a signal that would respond generally in the band gap of the asphaltenes, it is now known that the signals from most refined hydrocarbon materials are not enhanced by the presence of an iodine solution whereas the signals from unrefined hydrocarbons, and particularly the asphaltene based signals, are enhanced by the presence of iodine. Electron spin resonance signals may be derived from the heavy ends of refined products such as residuum or possibly from some heavy gas oils, but will not be derived from diesel, gas, butane or other lights ends. Because of this phenomenon, it is now possible to distinguish electron spin resonance signals from crude oil from electron spin resonance signals from most refined products, coal, shale, and algalmats, and, because it is possible to measure the amount of enhancement, it is possible to make a quantitative interpretation of the amount of hydrocarbon materials present in the sample.

FIGS. 3 and 4 illustrate electron spin resonance signals from crude oils (FIG. 3) and from refined products (FIG. 4). As illustrated in FIG. 3, the electron spin resonance signal 20 is a signal from crude oil materials deposited on an earth formation sample. This signal has an illustrated height h, representing the maximum positive and negative swing of the signal as the sample is subjected to an increasing frequency. Signal 21 represents the signal from the same sample measured after the sample has been subjected to a solution of iodine materials and illustrates the enhancement of the signal due to the presence of the iodine. In this case, the signal has an amplitude represented by letter H. The signals shown in FIG. 3 are portions of actual signals measured from crude oil in an earth formation sample.

FIG. 4 represents an electron spin resonance signal 30 measured from a refined hydrocarbon product and the same signal 31 measured from the same refined product with the addition of a solution of iodine materials. It should be noted that little, if any, enhancement has occurred in the signal from the refined product. The curves of FIG. 4 are actual curves measured on refined products.

In accordance with the present invention, a method is disclosed for exploring for and mapping the subsurface migration course of crude petroleum with the steps of collecting samples from subsurface formations, subjecting the samples to electron spin resonance signals to identify the presence of asphaltene materials, and then subjecting the samples that do respond with the desired electron spin resonance signals to an iodine solution environment so as to enhance the previously measured signal and to produce a distinguishing signal. Having accumulated the information concerning the subsurface formations and the enhancement of the electron spin resonance signals, the samples are then identified in location with respect to the subsurface formation and a course of potential migration or source of generation hydrocarbon crude is predicted so as to locate the possibility of a subsurface reservoir. In the ideal case, the migration path will be well identified and the source of the crude will be established.

We have further discovered a method for eliminating conflicting electron resonance spin signals from earth formation materials that can obscure the desired signal from petroleum crude. It is known that electron spin resonance signals from manganese falls in the same frequency range as the signals from petroleum crude. Furthermore, we have found that if manganese is present in an earth formation, it will be present in carbonate form. When measuring signals on an earth formation sample, if the signal from petroleum crude is weak, because only traces of curde are present, and if the formation contained carbonates, a signal from manganese may likely obscure the signal from the petroleum crude. In such a case, an acid wash of the earth formation sample will remove the carbonate and will remove the manganese with the carbonate. An acid wash with hydrochloric acid, or other suitable acids, will accomplish the desired result. The acid wash will not remove the petroleum crude, therefore electron spin resonance signals from the traces of crude will remain and, with the addition of the previously described iodine solution, will be enhanced.

In the copending application of S. W. Nicksic, Serial No. 202,102, filed Oct. 30, 1980, Now U.S. Pat. No. 4,415,671, there is a further disclosure of a procedure to provide additional evidence of the origin of electron spin resonance signals as derived from petroleum crude. In that application, it is shown that petroleum crude electron spin resonance signals will be suppressed when the petroleum crude is subjected to the presence of ferric chloride. Ferric chloride may be applied in a solution of benzene, toluene, xylene or carbon tetrachloride. Applying that disclosure to the present invention, it is possible to have a further exploration step for positively identifying electron spin resonance signals as signals from petroleum crude. That is, signals that were enhanced by the presence of iodine, will be suppressed by the presence of ferric chloride and if both enhancement and suppression occur, there is substantially conclusive evidence that the signals are from petroleum crude. The exploration method of the present invention may more conclusively resolve that petroleum crude is or was present in the earth formation sample.

While certain preferred methods of performing the invention have been specifically disclosed, it should be understood that the invention is not limited thereto as many variations will be readily apparent to those skilled in the art and the invention is to be given its broadest possible interpretation within the terms of the following claims.

What is claimed is:

1. An exploration method for mapping the subsurface course of crude petroleum accumulated in a producible subsurface reservoir by distinguishing crude petroleum based electron spin resonance signals from electron spin resonance signals from other constituent materials in earth formation samples, comprising the steps of:
   (a) collecting samples of subsurface earth formation materials from known positions within a formation from wells having known locations;
   (b) subjecting said earth formation samples to suitable conditions for the establishment of electron spin resonance of electrons present in said samples, and detecting electron spin resonance signals from said samples;

(c) selecting those earth formation samples from which said electron spin resonance signals were detected and contacting said selected samples with a solution containing iodine;

(d) subjecting said selected and contacted samples to said suitable conditions for establishment of electron spin resonance of electrons present in said samples, and detecting electron spin resonance signals from said selected samples;

(e) identifying from said first selected samples those earth formation samples from which enhanced electron spin resonance signals were detected attributable to said contacting with said solution containing iodine as samples containing electrons associated with crude petroleum;

(f) mapping the presence of said crude petroleum materials;

(g) producing a representation of potential migration paths of hydrocarbon crudes within said formation; and (h) locating the origin of said identified samples demonstrating said enhanced electron spin resonance signals in distance, direction and depth with respect to said subsurface reservoir by using said mapped potential migration paths.

2. The method of claim 1 with the additional step of subjecting samples identified as containing petroleum crude to the presence of ferric chloride to suppress electron spin resonance signals from petroleum crude.

* * * * *